(12) United States Patent
Barefield, II et al.

(10) Patent No.: US 9,664,212 B2
(45) Date of Patent: May 30, 2017

(54) EVALUATING A VESSEL FOR SUITABILITY FOR CONTAINING FLUID

(71) Applicants: James E. Barefield, II, Los Alamos, NM (US); Elizabeth J. Judge, Los Alamos, NM (US); Loan A. Le, Los Alamos, NM (US); Leon N. Lopez, Santa Cruz, NM (US); Andrew C. Beveridge, Los Alamos, NM (US); Daniel R. Chapman, Oakland, CA (US); Seth T. Taylor, Fullerton, CA (US)

(72) Inventors: James E. Barefield, II, Los Alamos, NM (US); Elizabeth J. Judge, Los Alamos, NM (US); Loan A. Le, Los Alamos, NM (US); Leon N. Lopez, Santa Cruz, NM (US); Andrew C. Beveridge, Los Alamos, NM (US); Daniel R. Chapman, Oakland, CA (US); Seth T. Taylor, Fullerton, CA (US)

(73) Assignees: CHEVRON U.S.A. INC., San Ramon, CA (US); LOS ALAMOS NATIONAL SECURITY, LLC, Los Alamos, NM (US)

(*) Notice: Subject to any disclaimer, the term of this patent is extended or adjusted under 35 U.S.C. 154(b) by 23 days.

(21) Appl. No.: 14/638,872

(22) Filed: Mar. 4, 2015

(65) Prior Publication Data

US 2016/0258815 A1 Sep. 8, 2016

(51) Int. Cl.
*G01J 3/30* (2006.01)
*F16B 2/08* (2006.01)
(Continued)

(52) U.S. Cl.
CPC ............. *F16B 2/08* (2013.01); *G01N 21/718* (2013.01); *G01N 21/274* (2013.01); *G01N 21/909* (2013.01); *G01N 2201/0221* (2013.01)

(58) Field of Classification Search
CPC . G01J 3/443; G01J 3/30; G01N 21/25; G01N 21/27; F16B 2/08; H01S 3/00
See application file for complete search history.

(56) References Cited

U.S. PATENT DOCUMENTS 6,407,811 B1 * 6/2002 Snyder ............... G01N 21/9501
356/237.3

OTHER PUBLICATIONS

"Improved LIBS limit of detection of Be, Mg, Si, Mn, Fe and Cu in aluminum alloy samples using a portable Echelle spectrometer with ICCD camera", Optics & Laser Technology 40 (2008) 30-38 by Walid Tawfik Y. Mohamed.*

(Continued)

*Primary Examiner* — Tarifur Chowdhury
*Assistant Examiner* — Jamil Ahmed
(74) *Attorney, Agent, or Firm* — King & Spalding LLP

(57) ABSTRACT

A method for evaluating a vessel for suitability to contain a fluid includes providing a vessel and forming a polished surface portion of the vessel by removing oxidation and/or contaminants from a portion of the vessel. The method further includes applying a focused laser to the polished surface portion to form plasma on the polished surface portion, and determining whether the vessel is suitable for containing a fluid based on silicon content of the polished surface portion. The silicon content is estimated based on light emitted from the plasma.

15 Claims, 9 Drawing Sheets

(51) Int. Cl.
*G01N 21/71* (2006.01)
*G01N 21/27* (2006.01)
*G01N 21/90* (2006.01)

(56) References Cited

OTHER PUBLICATIONS

Radziemski et al., "A brief history of laser-induced breakdown spectroscopy: From the concept of atoms to LIBS 2012", Spectrochimica Acta Part B, 2013, vol. 87, pp. 3-10.
Ismail et al., "LIBS limit of detection and plasma parameters of some elements in two different metallic matrices", J. Anal At. Spectrom., 2004, vol. 19, pp. 494-494.
Sun et al. "Determination of Mn and Si in iron ore by laser-induced plasma spectroscopy", Analytica Chimica Acta, 2000, vol. 413, pp. 187-195.
Walid Tawfik Y. Mohamed, "Improved LIBS limit of detection of Be, Mg, Si, Mn, Fe, and Cu in aluminum alloy samples using a portable Echelle spectrometer with ICCD camera", Optics & Laser Technology, 2008, col. 40, pp. 30-38.
Rusak et al. "Fundamentals and Applications of Laser-Induced Breakdown Spectroscopy", Critical Reviews in Analytical Chemistry, 1997, vol. 27, No. 4, pp. 257-290.

* cited by examiner

_US 9,664,212 B2_

EVALUATING A VESSEL FOR SUITABILITY FOR CONTAINING FLUID

ACKNOWLEDGMENT OF GOVERNMENT SUPPORT

This invention was made with government support under Contract No. DE-AC52-06NA25396 awarded by the U.S. Department of Energy. The government has certain rights in the invention.

PARTIES TO JOINT RESEARCH AGREEMENT

The research work described here was performed under a Cooperative Research and Development Agreement (CRADA) between Los Alamos National Laboratory (LANL) and Chevron under the LANL-Chevron Alliance, CRADA number LA05C10518-PTS-34.

FIELD OF INVENTION

The present disclosure generally relates to evaluating vessels, such as fluid vessels, for suitability for containing fluid based on silicon content.

BACKGROUND

In oil/gas and petrochemical industries, vessels (e.g., pressure containing equipment) are often used to store or transport fluids (i.e., liquids and/or gases). Some of these vessels may experience corrosion because of the corrosiveness of some of the fluids the vessels contain. For example, a pipe or another container used in sulfidation services may be exposed to sulfur compounds present in oil. Sulfur compounds may corrode the pipe and result in damage to the pipe. A damaged pipe may result in leakage of fluids and disruption of operations at a facility (e.g., an oil refinery).

Evaluating a vessel (new or used) prior to the actual use of the vessel to contain (e.g., store or transport) a corrosive fluid may avoid premature damage to the vessel and thus avoid disruption of operations. Also, evaluating whether a vessel (e.g., a pipe) that is in use as a container (e.g., storage or transportation) for a corrosive fluid is suitable for a continued use may allow timely replacement of the vessel and avoid disruption of operations due to unexpected damage to the vessel. Thus, a process and apparatus for evaluating a vessel for suitability to contain a fluid may be desirable.

SUMMARY

The present disclosure generally relates to evaluating vessels, such as fluid vessels, for suitability for containing fluid based on silicon content. In an example embodiment, a method for evaluating a vessel for suitability to contain a fluid includes providing a vessel and forming a polished surface portion of the vessel by removing oxidation and/or one or more contaminants from a portion of the vessel. The method further includes applying a focused laser to the polished surface portion to form plasma on the polished surface portion, and determining whether the vessel is suitable for containing a fluid based on silicon content of the polished surface portion. The silicon content is estimated based on light emitted from the plasma.

In another example embodiment, a mounting apparatus for a laser device includes a sleeve having a first opening and a second opening that are on opposite ends of the sleeve. A wall of the sleeve defines a cavity of the sleeve for positioning a probe head of the laser device. The mounting apparatus further includes a cable. A first portion of the cable is attached to the sleeve on a first side of the sleeve, and a second portion of the cable is attachable to the sleeve on a second side of the sleeve such that a third portion of the cable extends around a portion of the vessel when the second portion of the cable is attached to the sleeve. The second side of the sleeve is opposite the first side of the sleeve. The mounting apparatus also includes an attachment screw extending through the wall of the sleeve into the cavity to secure the probe head of the laser device within the cavity.

In another example embodiment, a method for evaluating a vessel for suitability to contain a fluid includes placing a sleeve of a mounting apparatus in contact with a vessel and extending a cable around the vessel from a first side of the sleeve to a second side of the sleeve. A first portion of the cable is attached to the sleeve on the first side of the sleeve. The method further includes attaching a second portion of the cable to the sleeve on the second side of the sleeve. The method also includes placing a probe head of a laser device in the sleeve such that a tip of the probe head is in contact with the vessel through an opening of the sleeve. The method further includes tightening the cable by moving the second portion of the cable in a direction away from the opening of the sleeve. The method also includes applying a laser to a polished surface portion of the vessel to form plasma, and determining whether the vessel is suitable for containing a fluid based on silicon content of the polished surface portion. The silicon content is estimated based on light emitted from the plasma.

These and other aspects, objects, features, and embodiments will be apparent from the following description and the claims.

BRIEF DESCRIPTION OF THE DRAWINGS

Various aspects of the invention will now be described with reference to the following figures in which the same reference numerals are used to designate corresponding parts throughout each of the several views.

Figure 1:
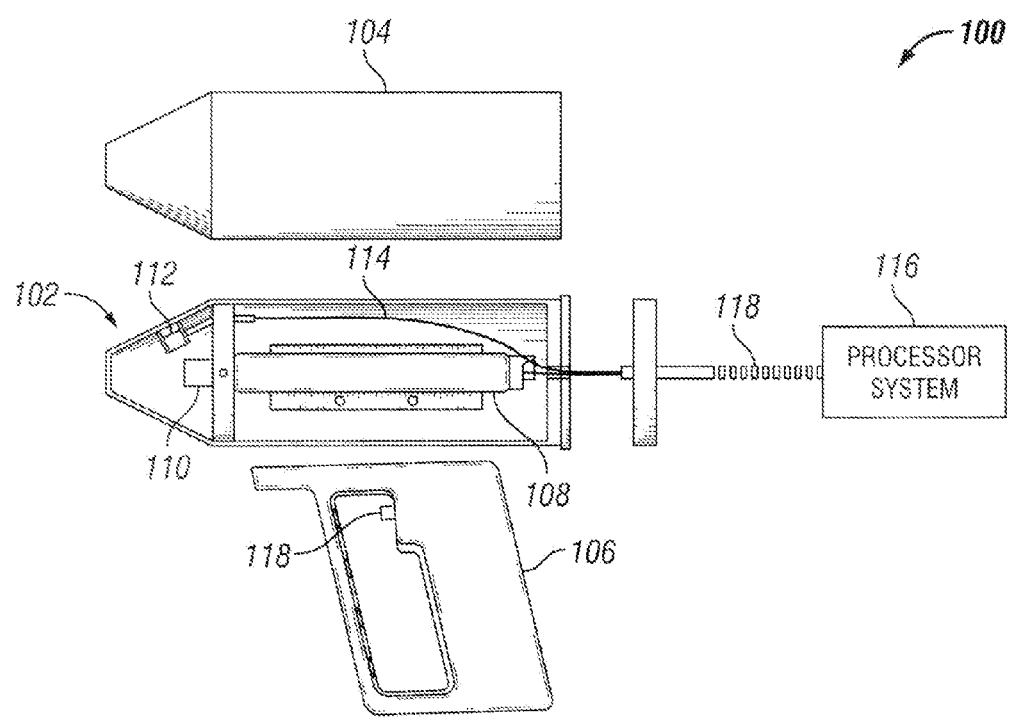
FIG. 1 illustrates a partially exploded view of a portable laser device for evaluating a vessel for suitability to contain a fluid based on silicon content of the vessel according to an example embodiment.

The drawings illustrate only example embodiments and are therefore not to be considered limiting in scope. The elements and features shown in the drawings are not necessarily to scale, emphasis instead being placed upon clearly illustrating the principles of the example embodiments. Additionally, certain dimensions or placements may be exaggerated to help visually convey such principles. In the drawings, reference numerals designate like or corresponding, but not necessarily identical, elements.

DETAILED DESCRIPTION OF THE EMBODIMENTS

In general, a vessel, such as a pipe, that is used in oil/gas and petrochemical industries should be suitable to contain fluids (i.e., liquids and/or gases) (e.g., oil) that are common in these industries. A vessel may be any pressure containing equipment. For example, a vessel may be any plan equipment such as piping, heat changers, pressure vessels, etc. In some example embodiments, a vessel may include several components. For example, a pipe may include many pieces of pipe, elbows, etc. that are, for example, welded together. In some cases, a vessel may be corroded over time because of, for example, chemical reactions between the material(s) used to make the vessel and a fluid contained in the vessel. With regard to a vessel, such as a pipe, that is already in use as a container for a corrosive fluid, the vessel or a portion of the vessel may be located above ground and in hard to reach locations. For example, in oil refineries, pipes used to contain oil may be located at elevations exceeding a hundred feet above the ground with narrow staircases providing access to the pipes. Evaluating pipe suitability for services, such as sulfidation services, in hard to reach locations may be challenging.

Turning to the drawings, FIG. 1 illustrates a partially exploded view of a portable laser device 100 for evaluating a vessel for suitability to contain a fluid based on silicon content of the vessel according to an example embodiment. For example, the portable laser device 100 may be used to evaluate a vessel's susceptibility to corrosion. To illustrate, for a safe use of a vessel (e.g., a pipe) as a container (e.g., storage or transportation) of a fluid, the vessel may need to be made from a material that has at least (i.e., equal to or greater than) a threshold weight percent of silicon. For example, in sulfidation services involving a fluid (e.g., oil) that contains a corrosive compound (e.g., sulfur), a carbon-steel pipe or another carbon-steel container may need to have at least 0.10 weight percent of silicon to safely contain the fluid. The portable laser device 100 may be used to evaluate whether a vessel is suitable to contain a fluid based on the threshold weight percent of silicon that vessel is expected to have for safe operations. For example, the portable laser device 100 may be used to evaluate a vessel's susceptibility to corrosion.

As illustrated in FIG. 1, the laser device 100 may include a probe head 102 having a cover 104 (shown removed from the probe head). The laser device 100 may also include a handle 106 for gripping the laser device 100 with a hand. The laser device 100 may include a processor system 116 that is connected to the probe head 102 via a connection 118. The connection 118 may contain one or more wires (e.g., a 15 wire electrical cable) and fiber optic cable.

In some example embodiments, the probe head 102 includes a laser source 108 that generates a plasma and light collection optics 112. For example, the laser source 108 may generate one or more laser pulses in response to a user pressing on a trigger 118 on the handle 106. In some example embodiments, the laser source 108 may be a Nd-YAG laser. The probe head 102 further includes a focusing lens 110 that focuses the laser onto a target (e.g., a pipe). The plasma produced by the laser source 108 is intended to interact with a surface portion of the target, resulting in plasma that includes atoms of the chemical elements that make up the target. The atoms, which are in an excited energy state, may lose energy in the form of emitted light. The light emitted by the plasma may enter the light collection optics 112. The light from the plasma that enters through the light collection optics 112 travels through a fiber optic cable 114 to the processor system 116, which includes a spectrometer that generates a spectrum of the light from the plasma. The spectrometer separates the light from the plasma into component wavelengths. A detector (e.g., a charge coupled detector ("CCD")) coupled to the spectrometer may transmit electrical signals to a computer/processor of the processor system 116 for processing of the spectral information and provide information related to the chemical elements present in the plasma and their weight percentages based on information, for example, stored in the processing system.

The apparatus includes a laser (e.g., Nd-YAG laser) and focusing optics that focus the laser beam produced from the laser to a sample. The beam interacts with the sample and forms light-emitting plasma. Light emitted from the plasma is directed through an optical fiber to a spectrograph, which separates the light into component wavelengths, and then to a detector (e.g., a charge coupled detector ("CCD")) which transmits electrical signals to a computer/processor of the processing system configured to provide information related to the chemical elements present in the plasma and their weight percentages.

In some example embodiments, the processor system 116 may be stored in a backpack that can be carried by a person. The processor system 116 may include a processor that analyzes spectra and other processing functions and a battery that provides power to the laser device 100. Using battery as a power source can eliminate the need for locating power outlets (which may not be readily available and/or conveniently located) and the need for extending power extension cords, in some cases, for long distances.

In some example embodiments, the processor system 116 may also include a power supply, a delay generator, a USB hub, and electrical connections for power distribution.

In some example embodiments, the laser device 100 is provided with safety features that prevent the laser source 108 from firing even when the trigger 118 is depressed. For example, the laser device 100 may include LED (light emitting diode) indicators that indicate that the laser source is ready to fire. The laser device 100 may also include a safety interlock that is engaged, for example, when a tip of the probe head 102 is pressed against a target such as a pipe. The laser source 108 may fire only if the safety interlock is engaged. The laser device 100 may also include an interlock reset feature, which is actuated with an interlock reset button that may be located at the underside of the handle 106. A laser ready LED indicator light may change, for example, from red to green, to indicate that the safety interlock is engaged and the laser source 108 is safe to fire using, for example, the trigger 118. The number of laser pulses that are generated by the laser source 108 in response to depressing of the trigger 118 may be programmed in the processor system 116. To illustrate, a single press on the trigger 118 may result in one or more laser pulses being fired by the laser source 108. For example, a single press on the trigger 108 may result in 10 laser pulses being are fired by the laser source 108.

In some example embodiments, the laser device 100 may be programmed such that one or more spectra of the background (i.e., without firing laser pulses) are taken. For example, a background spectrum may be used to improve the quality of the spectrum of light generated after a laser pulse is fired. To illustrate, spectral components of light present prior to the firing of a laser pulse may be subtracted from the spectrum of light collected through the collection optics 112 after a laser pulse is fired. Further, by generating a light spectrum after each laser pulse is fired, the multiple spectra corresponding to the multiple laser pulses may be processed by the processing system 116 to produce a more reliable spectrum of the light emitted by the plasma.

Figure 3A:
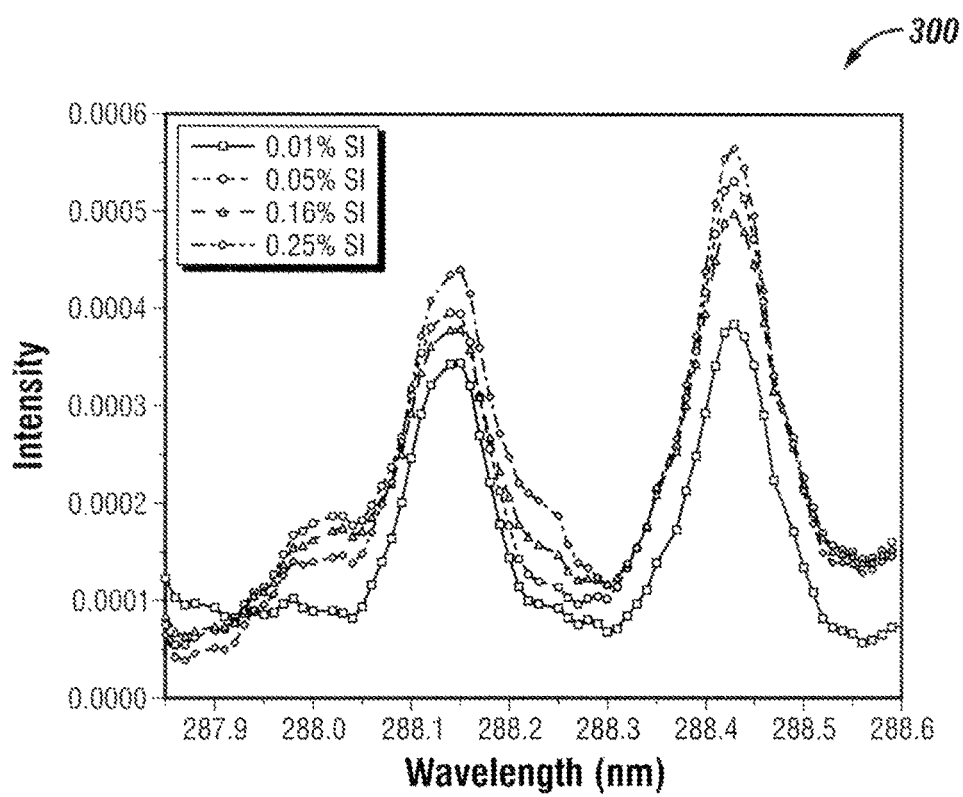
FIG. 3A illustrates a plot of emission spectra generated from the light emitted by the plasma formed using the portable laser device of FIG. 1, corresponding to different weight percentages of silicon in a vessel made of carbon steel according to an example embodiment.
Figure 3B:
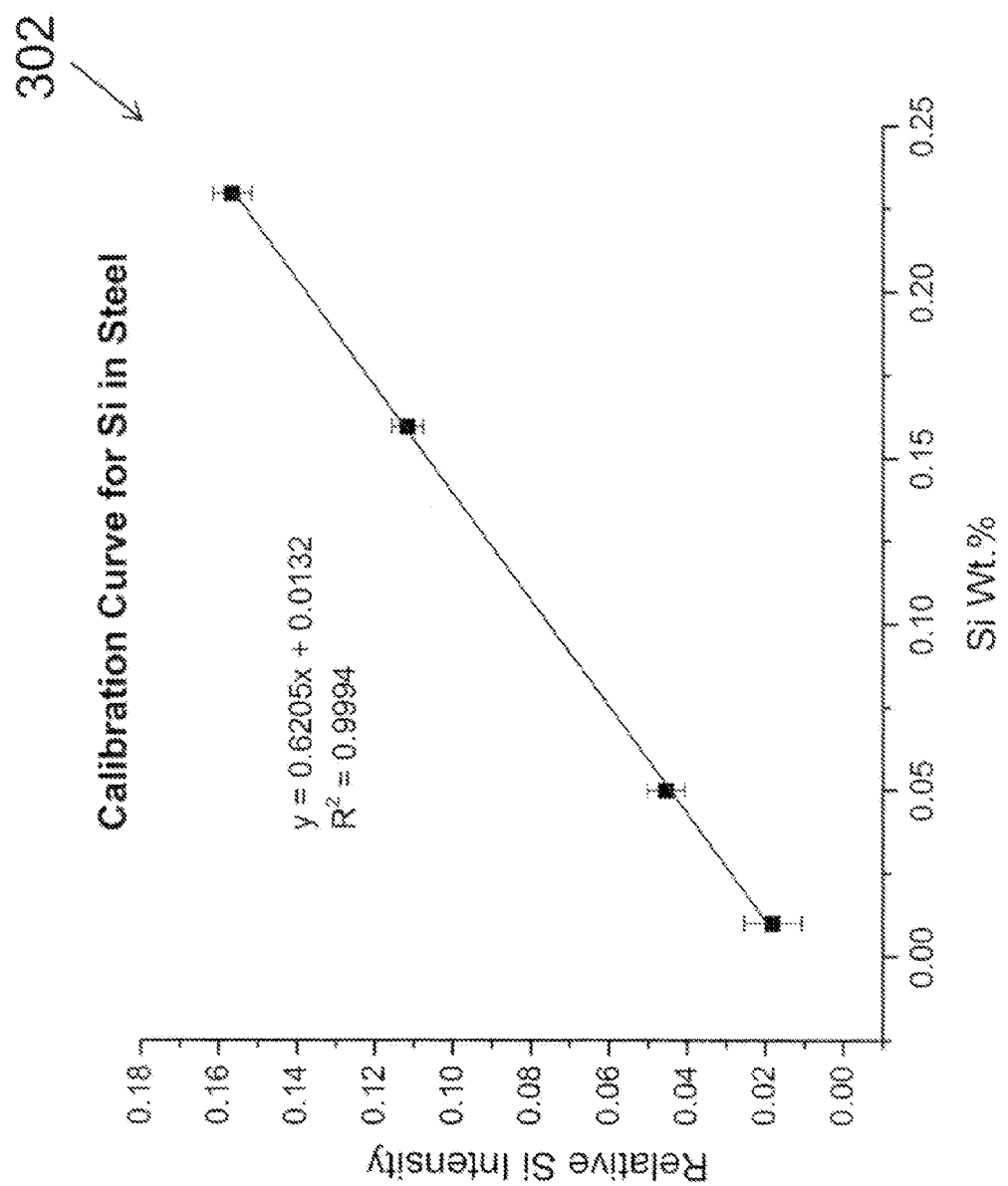
FIG. 3B illustrates a calibration curve generated from the emission spectra shown in 3A.

To evaluate a vessel for suitability to contain a fluid based on silicon content of the vessel, a spectrum of the light emitted by the plasma may be evaluated relative to spectra generated based on samples with known amounts of silicon content. For example, a spectrum may be generated for light emitted from plasma by applying a laser, using the portable laser device 100, to samples that have known weight percentages of silicon. A calibration curve may be generated from the spectra that correspond to the different weight percentages of silicon. An example of emission spectra is shown in FIG. 3A. A calibration curve generated from the emission spectral is shown in FIG. 3B. To estimate the silicon content of a vessel with unknown silicon content, a spectrum of light emitted by plasma formed by applying a laser to a polished portion of the vessel may be compared against the plot of calibration curves. For example, the polished surface portion may be greater than 300 microns. The laser is applied to a fraction of the polished surface portion. The spectrum of the light emitted by plasma formed by applying the laser to the polished portion of the vessel may be generated by the processing system 116 as described above.

Because the laser device 100 is portable, vessels such as pipes in an oil refinery that are hard to reach may be evaluated to estimate silicon content of the vessels. By estimating the weight percentages of silicon in the vessels, one or more vessels that do not have a threshold weight percent of silicon may be replaced in a manner that avoids unexpected leaks and accidents. Further, new vessels can also be evaluated in a similar manner prior to deployment for use. For example, a carbon-steel pipe or another carbon-steel container that is or will be used in sulfidation services involving a fluid (e.g., oil) that contains a corrosive compound (e.g., sulfur) may be evaluated to determine whether the pipe/container has at least 0.10 weight percent of silicon. Use of the laser device 100 is made significantly easier because the required sizes of the polished surface portion and the area of the polished surface portion to which the laser needs to be applied are relatively small.

Use of laser based spectroscopy for detection of elements is described in Radziemski et al., "A brief history of laser-induced breakdown spectroscopy: From the concept of atoms to LIBS 2012," Spectrochimica Acta Part B, 2013, vol. 87, pp. 3-10; Ismail et al., "LIBS limit of detection and plasma parameters of some elements in two different metallic matrices," J. Anal. At. Spectrom., 2004, vol. 19, pp. 489-494; Sun et al., "Determination of Mn and Si in iron ore by laser-induced plasma spectroscopy," Analytica Chimica Acta, 2000, vol. 413, pp. 187-195; Improved LIBS limit of detection of Be, Mg, Si, Mn, Fe, and Cu in aluminum alloy samples using a portable Echelle spectrometer with ICCD camera," Optics & Laser Technology, 2008, vol. 40, pp. 30-38; Rusak et al., "Fundamentals and Applications of Laser-Induced Breakdown Spectroscopy," Critical Reviews in Analytical Chemistry, 1997, vol. 27, no. 4, pp. 257-290, the contents of which are incorporated by reference herein.

In some example embodiments, the laser device 100 may be used in the evaluation of a vessel at various temperatures including elevated temperatures (e.g., greater than 400° F.), which has the benefit of avoiding shutting down or delaying operations.

Although the laser device 100 is shown to have a particular shape, in alternative embodiments, the laser device 100 may have other shapes without departing from the scope of this disclosure. In some alternative embodiments, the trigger 118 may be omitted such that triggering the laser device is performed remotely via a wired or wireless connection. Further, the processing system 116 may be located close to the probe head 102, such as in a backpack carried by a person operating the trigger 118, or some components or the entire processing system 116 may be located remotely from the probe head 102.

Figure 2:
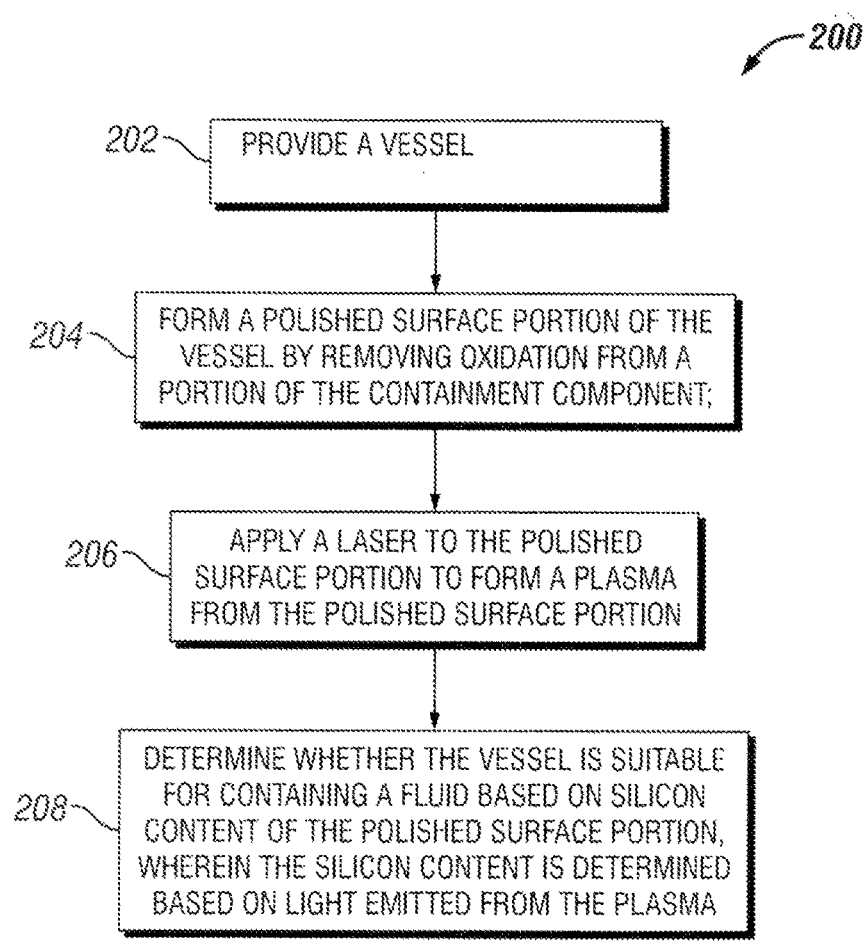
FIG. 2 illustrates a flow chart of a method for evaluating a vessel for suitability to contain a fluid based on silicon content of the vessel using the portable laser device of FIG. 1 according to an example embodiment.

FIG. 2 illustrates a flow chart of a method 200 for evaluating a vessel for suitability to contain a fluid based on silicon content using the portable laser device of FIG. 1 according to an example embodiment. The method 200 includes providing a vessel, at step 202. The vessel may be made from a material that includes silicon or may be suspected to include silicon. For example, the vessel may be a pipe or another container that may be already in use or will be used to store or transport a fluid. For example, a pipe used in sulfidation services in oil refineries may be made from carbon steel. The major component of such pipes is iron. Minor components of these pipes are other elements such as manganese, phosphorus, sulfur, silicon, chromium, copper, molybdenum, nickel, and vanadium. Table 1 summarizes the weight percentages (wt. %) of minor components present in three example grades of carbon steel, specifically for ASTM A106 materials called Standard Specification for Seamless Carbon Steel Pipe for High-Temperature Service.

| Element | Grade A | Grade B | Grade C |
| --- | --- | --- | --- |
| Carbon, max (a) | 0.25 | 0.30 | 0.35 |
| Manganese | 0.27-0.93 | 0.29-1.06 | 0.29-1.06 |
| Phosphorus, max | 0.035 | 0.035 | 0.035 |
| Sulfur, max | 0.035 | 0.035 | 0.035 |
| Silicon, min | 0.10 | 0.10 | 0.10 |
| Chrome, max (b) | 0.40 | 0.40 | 0.40 |
| Copper, max (b) | 0.40 | 0.40 | 0.40 |
| Molybdenum b) | 0.15 | 0.15 | 0.15 |
| Nickel, max (b) | 0.40 | 0.40 | 0.40 |
| Vanadium, max (b) | 0.08 | 0.08 | 0.08 |

Adjustments to the values in Table 1 may be made for achieving an acceptable grade of steel based upon the relative amounts of some of the elements. For example, in Table 1, first column, first row, for the element carbon, for each reduction of 0.01% below the specified maximum, an increase of 0.06% manganese is permitted up to a maximum of 1.35% for the ASTM A106 specification. In addition, the weight percentage collectively for the last five entries, i.e., chrome, copper, molybdenum, nickel, and vanadium, should not exceed 1% the ASTM A106 specification. The ASTM A106 specification of carbon steel may be suitable for service involving the containment of oil inside a pipe typically at elevated temperatures (e.g., a temperature greater than 400.° F.)

An example grade of carbon steel for a containment pipe at an oil refinery is ASTM A106 Grade B. As Table 1 indicates, Grade B steel should have a minimum weight percent of silicon of 0.10. The method 100 may be used to evaluate whether a carbon steel pipe expected to contain a particular amount of silicon, does include at least 0.10 weight percent of silicon.

At step 204, the method 100 includes forming a polished surface portion of the vessel by removing oxidation from a portion of the vessel. For example, a small surface portion of a carbon steel pipe (e.g., 1 centimeter in diameter) may be polished using a polisher to remove oxidized layers from the pipe. In some example embodiments, the polished surface portion may be formed by removing oxidation and/or contaminants from a portion of the vessel. At step 206, the method 200 includes applying a focused laser to the polished surface portion to form plasma on the polished surface portion. In general, the laser is applied soon after the polished surface portion is formed to avoid substantial oxidation of the polished surface portion that can affect the results. For example, the portable laser device 100 of FIG. 1 may be used to fire one or more laser pulses at the polished surface portion of the vessel such as a carbon-steel pipe. The light emitted by the plasma formed on the polished surface portion after each laser pulse is collected by the collection optics 112 of the laser device 100.

In some example embodiments, when more than one laser pulse is fired per operation, spectra from the plasma may be processed (e.g., averaged) to generate a representative spectrum. Further, background spectra may be generated and subtracted from the spectrum of the light collected after the application of the laser to form the plasma.

To illustrate, intensity level of existing light prior to applying the focused laser to the polished surface portion may be determined and subtracted from intensity level of light collected, for example, by the collection optics 112 of FIG. 1 after applying the laser to determine the intensity level of the light emitted from the plasma.

In some example embodiments, applying the focused laser to the polished surface portion at step 206 includes applying a laser pulse once every three seconds. For example, ten pulses may be generated by the laser device 100 of FIG. 1 at every trigger of the laser source 108 of the laser device 100. Alternatively, fewer or more pulses may be generated by the laser device 100 of FIG. 1 at every trigger. For example, each laser pulse may have a pulse width of between 5 nanoseconds and 8 nanoseconds. In some example embodiments, each laser pulse may have approximately 25 millijoules of energy.

At step 208, the method 200 includes determining whether the vessel is suitable for containing a fluid based on silicon content of the polished surface portion. The silicon content is determined based on light emitted from the plasma. For example, the processor system 116 of FIG. 1 may be used to compare the spectral intensity of the light emitted by the plasma against a calibration curve (e.g., calibration curve shown in FIG. 3b) to estimate the weight percent of silicon in the polished surface portion of the vessel.

In some example embodiments, the method 200 may be performed on different sections of a vessel. To illustrate, a vessel may include several components. For example, a pipe may include many pieces of pipe, elbows, etc. that are, for example, welded together. Although a particular order of steps of the method 200 are shown in FIG. 2, in some alternative embodiments, the steps may be performed in a different order without departing from the scope of this disclosure.

Referring to FIGS. 2, 3A, and 3B, the emission spectra 300 shown in FIG. 3A were used to generate a calibration curve 302 shown in FIG. 3B, which may be used to estimate the silicon content of the polished surface portion formed at step 204 of the method 200. The calibration curve shown in FIG. 3B was generated (for example, by the laser device 100) based on components/samples containing known weight percents of silicon. To illustrate, FIG. 3B is generated from the spectra shown in 3A through data analysis which may include background subtraction, peak fitting of the iron and silicon emission features, intensity integration of fitted peaks, and ratio of Si/(Fe+Si) integrated intensity. The ratio is then plotted as a function of known Si weight percent. This data processing may be automated and completed for all the standards. The result is a calibration curve, as shown in FIG. 3B with a linear fit equation (y=mx+b) and correlation coefficient ($R^2$) calculated. Finally, a sample with unknown silicon content is measured and the Si/(Fe+Si) ratio is determined. This ratio is then used in the linear fit equation from the calibration curve to determine the weight percent of silicon.

As illustrated in FIG. 3A, different silicon spectral intensities correspond to different weight percentages of silicon. For example, silicon content of 0.01 weight percent is represented by one spectrum (i.e., an intensity vs wavelength curve), silicon content of 0.05 weight percent is represented by another spectrum, so on and on. Limiting the wavelength window to 280 nm to 302 nm allows a resolution needed for quantifying weight percent of silicon.

In some example embodiments, after determining the spectrum of light emitted by plasma formed by applying the laser at step 206, the spectrum may be evaluated relative to the calibration curve shown in FIG. 3B. To illustrate, the spectra in FIG. 3A have a shoulder peak (of a larger iron peak) appearing in a region between approximately 288.2 nm and approximately 288.3 nm. The literature value for Si atomic emission is 288.158 nm; however, spectral calibration for the spectrometer used to generate the emission spectra shown in FIG. 3A slightly shifted the Si emission to ~288.25 nm. The shoulder peak within the range of wavelength can be used to estimate the weight percent of silicon in carbon steel pipe or another carbon steel container. As illustrated in FIG. 3, the shoulder between approximately 288.2 nm and approximately 288.3 nm is more pronounced at higher weight percentages of silicon, but can be clearly seen in spectra corresponding to samples that have 0.05 and 0.16 weight percent silicon.

In general, intensity level of the light emitted by the plasma formed at the polished surface portion of the vessel in the wavelength range of approximately 288.2 nm to approximately 288.3 nm may be used to determine whether the silicon content of the polished surface portion is at least a threshold (e.g., 0.10) weight percent. The silicon weight percent of the polished surface portion may be considered as representative of the silicon weight percent of the vessel and may be used to determine whether the vessel is suitability to contain a fluid (e.g., oil) based in what is considered a safe weight percent (e.g., 0.10) of silicon.

In some example embodiments, the processor system 100 of FIG. 1 or another processor may quantify the silicon from the spectra by fitting the Gaussian peaks to the iron and silicon emission spectral features. In general, calibration curves may be generated based on known weight percentages of silicon at least once per use. Once the spectrum the light emitted by the plasma is determined, intensity level of the light emitted by the plasma as represented in the spectrum can be used to estimate the weight percent of silicon.

In some example embodiments, pipes made of carbon-steel that contain less than 0.10 weight percent of silicon and that are in use in a sulfidation service may need to be replaced with pipes that have at least 0.10 weight percent of silicon. Pipes made of carbon-steel that contain less than 0.10 weight percent of silicon should not be used in a sulfidation service. The method 200 can be used to estimate the weight percent of silicon in a vessel (e.g., a pipe) to evaluate whether the vessel is suitable for containing a fluid in a particular application such as sulfidation services based on expected safety threshold weight percent of silicon amount.

The method 200 may be implemented to evaluate whether the vessel (e.g., a ASTM A 106 Grade B carbon-steel pipe) is suitable for use in a particular application, while the vessel is in service at elevated temperatures (generally above 25° C.). For example, the temperature of the vessel may be 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C. or higher including 450° C. and above.

By evaluating whether a vessel is suitable for use to contain a fluid at elevated temperatures (e.g., greater than 400° F.), the method 200 may avoid shutting down of operations or delays in operations that may otherwise be required to evaluate the suitability of the vessel. Further, replacement vessels can be evaluated to determine suitability.

Although four spectra are shown in FIG. 3, in other embodiments, fewer or more than four spectra may be used in a plot of calibration curves for use to estimate a silicon content of a vessel.

Figure 4:
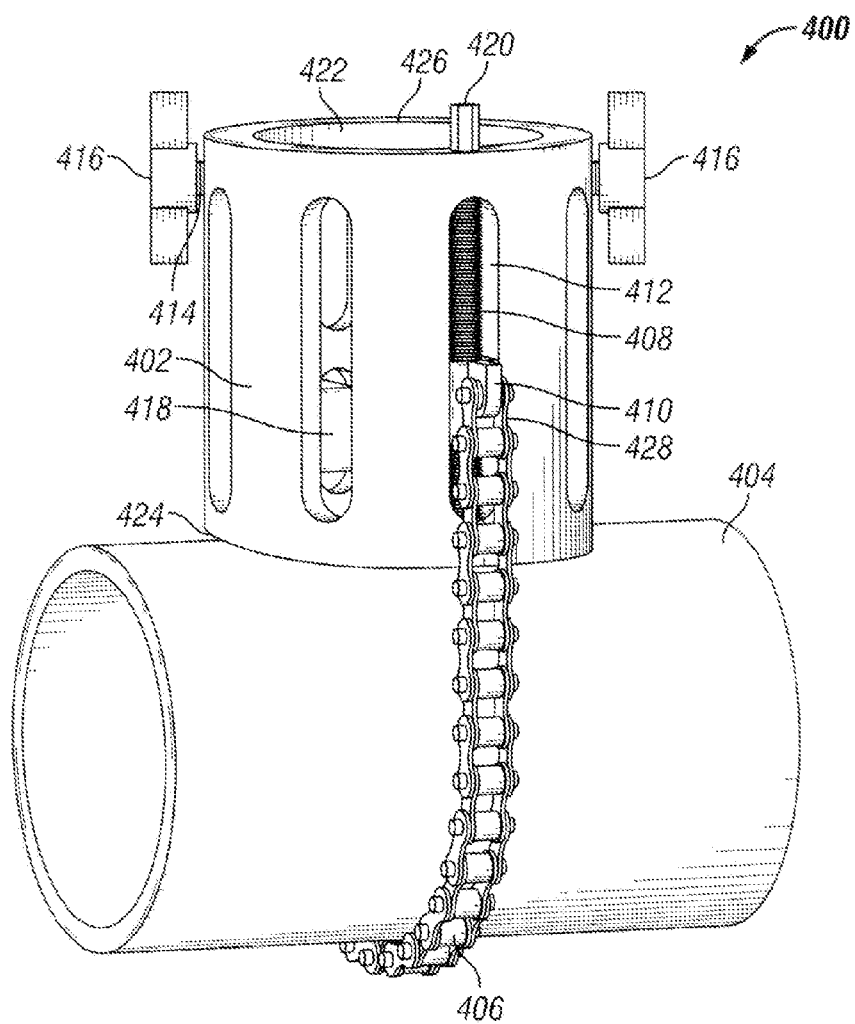
FIG. 4 illustrates a mounting apparatus for mounting the portable laser device of FIG. 1 to a vessel to be evaluated for silicon content according to an example embodiment.

FIG. 4 illustrates a mounting apparatus 400 for mounting the portable laser device 100 of FIG. 1 to a vessel 404 to be evaluated for silicon content according to an example embodiment. The mounting apparatus 400 includes a sleeve 402 and a chain 406. The sleeve 402 has a first opening 422 and a second opening 424 that are on opposite ends of the sleeve 402. A wall of the sleeve defines a cavity 426 of the sleeve 402 for positioning a probe head 102 of the laser device 100.

In some example embodiments, a first portion of the chain 406 is attached to the sleeve 402 on a first side of the sleeve 402, and a second portion 428 of the chain 406 is attachable to the sleeve 402 on a second side of the sleeve 402 such that a third portion of the chain extends around a portion of the vessel 404 when the second portion 428 of the chain 406 is attached to the sleeve 402. The first side and the second side of the sleeve 402 may be opposite sides of the sleeve 402. To illustrate, a first portion of the chain 406 may be attached to the sleeve 402 by a chain attachment device 418 that is, for example, fastened to the sleeve 402. The second portion 428 of the chain 406 may be attached the sleeve 402 by a chain attachment device 410. For example, the mounting apparatus 402 may include a length adjustment screw 408 that extends through the chain attachment device 410 such that the chain attachment device 410 is movable along the length adjustment screw 408 by rotating the length adjustment screw 408. As the chain attachment device 410 moves along the length adjustment screw 408, the second portion 428 of the chain 406 can move along with the chain attachment device 410. The chain 406 may be attached to the chain attachment device 410 using a fastener such as a screw or by inserting a protrusion in the chain attachment device 410 into a hole of the chain 406.

In some example embodiments, the length adjustment screw 408 may be attached to the sleeve 402 by extending through the wall of the sleeve 402. The length adjustment screw 408 may extend across a slot 412 formed in the wall of the sleeve 402 and may be attached to the sleeve 402 at the bottom end of the slot 412. In general, the length adjustment screw 408 is rotatable in a first direction to tighten the chain 406 around the portion of the vessel 404 and in a second direction to loosen the chain 406 of around the portion the vessel 404. To illustrate, a wrench or another tool may be attached to the top portion 420 of the length adjustment screw 408 to rotate the length adjustment screw 408. Thus, the sleeve 402 may be securely attached to the vessel 404 by placing the sleeve 402 on the vessel 404, extending the chain 406 around the vessel 404, attaching the chain 406 to the sleeve by securing the second portion 428 of the chain 406 to the chain attachment device 410, and rotating the length adjustment screw 408 to tighten the chain 406 around a portion of the vessel 404.

In some example embodiments, one or more attachment screws 414 extend through the wall of the sleeve 402 into the cavity 426 to secure the probe head 102 of the laser device 100 within the cavity 426. For example, a respective knob 416 may be attached to each attachment screw 414 to move the respective attachment screw 414 further into or away from the cavity 426.

Although a chain is shown in FIG. 4, in alternative embodiments, another cable that may, for example, include holes for attachment to the chain attachment device 410 may be used. Further, although the sleeve 402 is shown to have a cylindrical shape, in alternative embodiments, the sleeve 402 may have other shapes without departing from the scope of this disclosure. Further, in some alternative embodiments, the vessel 404 may have shapes other than shown in FIG. 4. For example, the vessel 404 may have at least one flat surface such that the sleeve 402 comes in contact with the flat surface of the vessel 404 instead of the curved surface shown in FIG. 4. In some example embodiments, the vessel 404 may be positioned in a different orientation such as a vertical orientation instead the horizontal orientation shown in FIG. 4.

Figure 5:
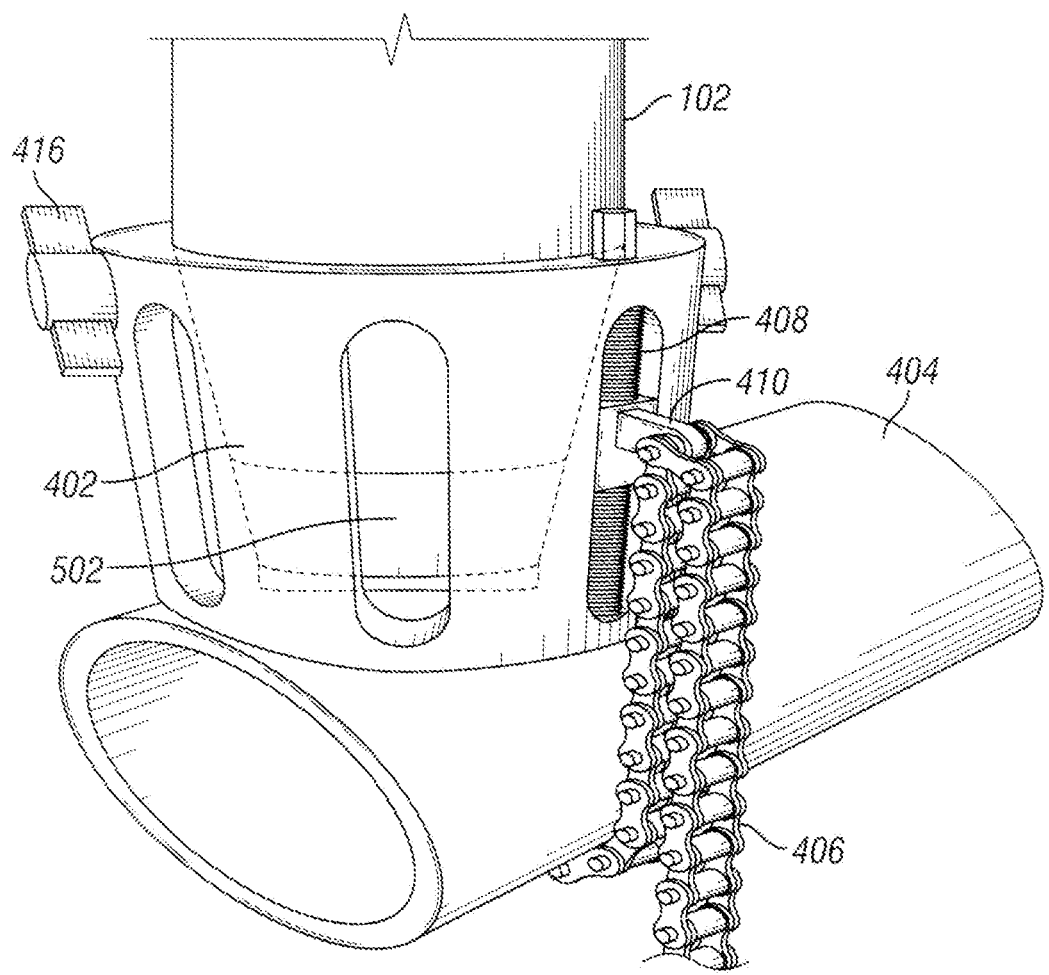
FIG. 5 illustrates a probe head of the portable laser device of FIG. 1 attached to the mounting apparatus of FIG. 4 for evaluating a vessel for silicon content according to an example embodiment.

FIG. 5 illustrates a probe head 102 of the portable laser device 100 of FIG. 1 attached to the mounting apparatus 400 of FIG. 4 for evaluating a vessel for silicon content according to an example embodiment. Referring to FIGS. 1, 4, and 5, in some example embodiments, after the mounting apparatus 400 is attached to the vessel 406 as described with respect to FIG. 4, the laser device 100 may be inserted in the cavity 426 of the sleeve 402 such that the tip of the probe head 102 of the laser device 100 is in contact with the vessel 404. To illustrate, an opening in the tip of the probe head may be lined up against a polished surface portion of the vessel 404 such that the laser device 100 of FIG. 1 may be used to apply a focused laser to the polished surface portion of the vessel. After the probe head 102 is positioned in the cavity 426 of the sleeve 402, the knobs 416 may be rotated to secure the probe head 102 within the cavity 426 of the sleeve 402 using the screws 414 shown in FIG. 4. In some example embodiments, after the probe head 102 is inserted in the cavity 426, the chain 404 may be tightened or loosened around the vessel 404 by rotating the length adjustment screw 408 such that the chain attachment device 410 moves along the length adjustment screw 408 depending on the direction of rotation.

In some example embodiments, a curved tip 502 may be attached to the tip of the probe head 102. To illustrate, the curved tip 502, instead of the probe head 102, may come in physical contact with the vessel 404. For example, the curved tip 502 may have a curved surface that has a radius of curvature that closely matches the radius of the vessel 404.

Figure 6:
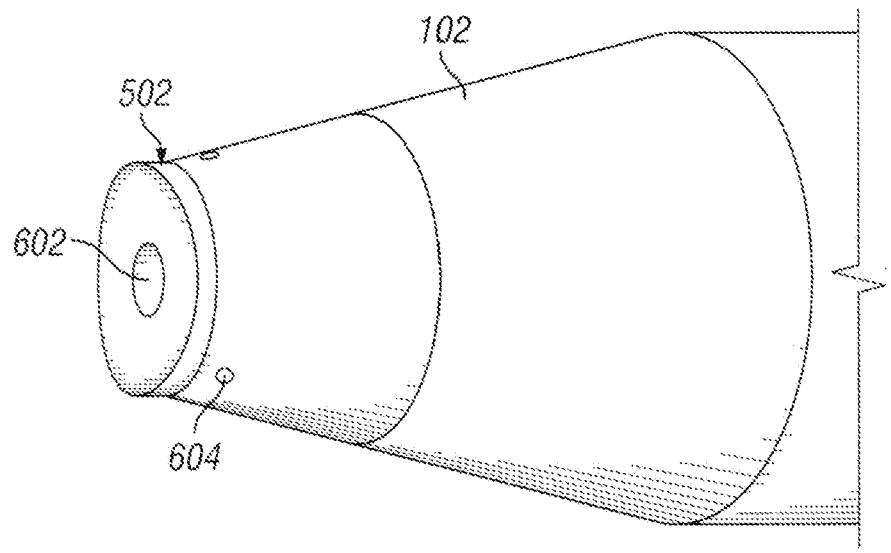
FIG. 6 illustrates a curved tip attached to a probe head of the portable laser device of FIG. 1 according to an example embodiment.
Figure 7:
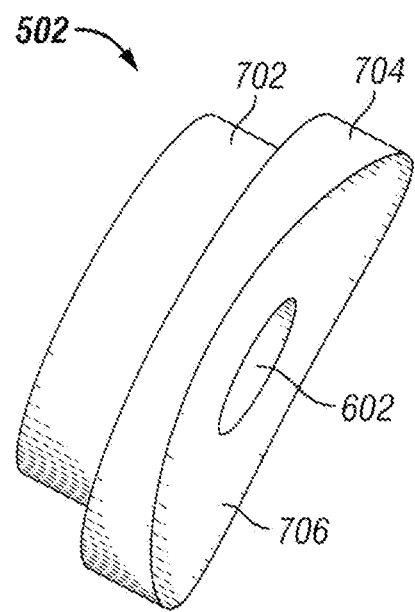
FIG. 7 illustrates a perspective view of the curved tip of FIG. 5 according to an example embodiment.

FIG. 6 illustrates a close up view of the curved tip 502 attached to the probe head 102 of the portable laser device 100 of FIG. 1 according to an example embodiment. FIG. 7 illustrates a perspective view of the curved tip 502 of FIG. 5 according to an example embodiment. Referring to FIGS. 6 and 7, in some example embodiments, the curved tip 502 is attached to the probe head 102 using one or more fasteners that are inserted in respective one or more holes 604 in the probe head 102. Alternatively, the curved tip 502 may be attached to the probe head 102 using other means such as threaded attachment. The curved tip 502 may be removable from the probe head 102 such that another curved tip 502 having a desired radius of curvature may be attached to the probe head 102.

Figure 8:
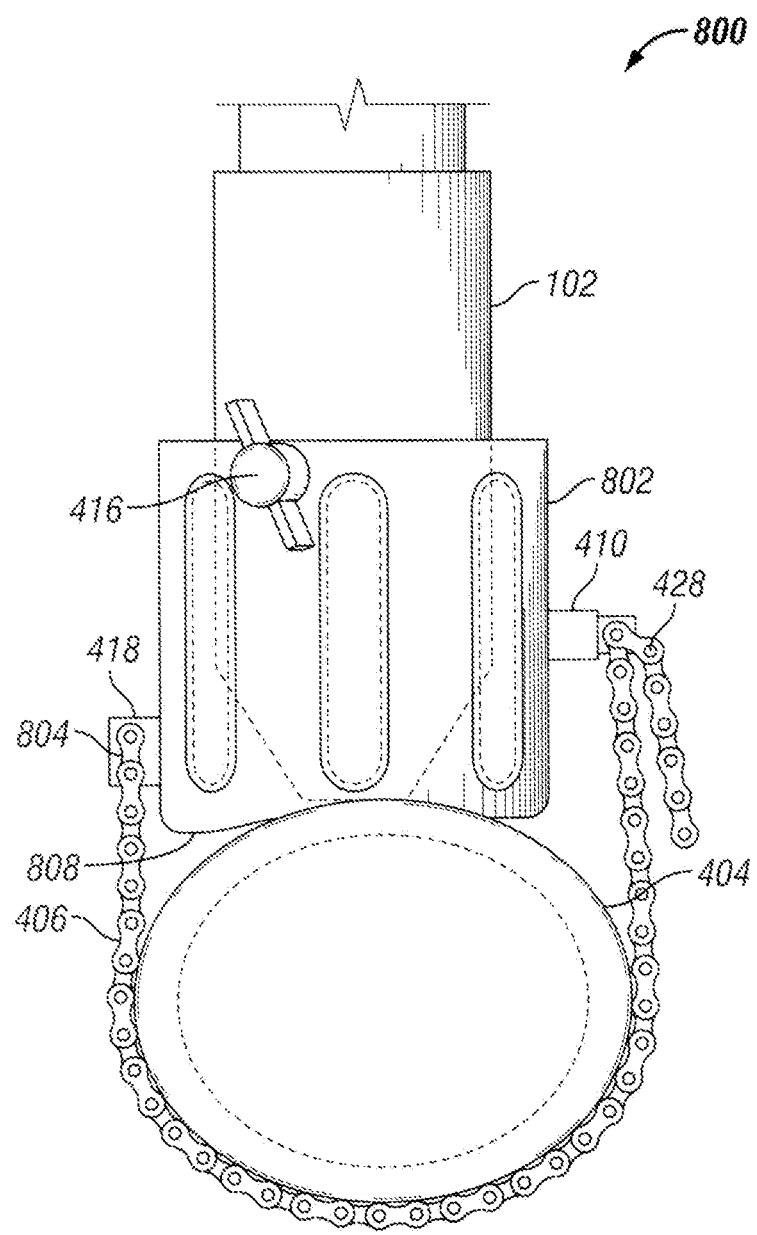
FIG. 8 illustrates a mounting apparatus for mounting the portable laser device of FIG. 1 to a vessel to be evaluated for silicon content according to another example embodiment.

In some example embodiments, the curved tip 502 may have a neck section 702 that is sized to fit in the opening of the probe head 102. The curved tip 502 may also have a broad section 704 having a curved surface 706. In general, the curved tip 502 may be selected for attachment to the probe head 102 based on matching between the radius of curvature of the surface 706 and the radius of the vessel 404. For example, the curved tip 502 may make a stable contact with a pipe and allow a steady use of the laser device 100. As illustrated in FIGS. 7 and 8, the curved tip 502 has a passageway 602 that extends through both the neck section 702 and the broad section 704 for applying a laser from the laser device 100 of FIG. 1 to a vessel. When the curved tip 502 is attached to the probe head 102, the passageway 602 may be positioned against a polished surface portion of the vessel 404 as shown, for example, in FIG. 4 such that laser from the laser device 100 of FIG. 1 can be applied to the polished surface portion and light from the plasma can enter the collection optics 112.

Although the curved tip 502 is shown in FIG. 7 as having particular shapes and relative dimensions, in alternative embodiments, the curved tip 502 may have other shapes and different relative dimensions.

FIG. 8 illustrates a mounting apparatus 800 for mounting the portable laser device 100 of FIG. 1 to the vessel 404 to be evaluated for silicon content according to another example embodiment. The mounting apparatus 800 is similar to and is used substantially in the same manner as the mounting apparatus 400 of FIG. 4. For the sake brevity, description of some elements of the mounting apparatus 800 that are described above is omitted here. In some example embodiments, the mounting apparatus 800 includes a sleeve 802. The sleeve 802 may have an end portion 808 that is curved. For example, the end portion 808 of the sleeve 802 may be curved such that at least a portion of the end portion 808 matches the curvature of the vessel 404, which allows for stable positioning of the sleeve 802 on the vessel 404.

As illustrated in FIG. 8, a first portion 804 of the chain 406 is attached to the chain attachment device 418. For example, the first portion 804 may be attached to the chain attachment device 418 using a fastener or another similar means. In some example embodiments, the chain attachment device 418 may be fixedly attached to the sleeve 802 to hold the first portion 804 of the chain 406 in a fixed position. As described with respect to FIG. 4, the chain attachment device 410 may move along the length adjustment screw 408 (shown in FIG. 4) or may otherwise move vertically up or down to tighten or loosen the chain 406 around the vessel 404. After the chain 406 is tightened around the vessel 404, the probe head 102 may be inserted in the cavity of the sleeve 802 such that the tip of the probe head 102 is in contact with the surface of the vessel 404. To illustrate, the opening in the tip of the probe head 102 may be positioned against a polished surface portion of the vessel 404 such that the laser device 100 of FIG. 1 may be used to apply a focused laser to the polished surface portion of the vessel and light from the plasma can enter the collection optics 112.

Although the chain 406 is shown in FIG. 8, in alternative embodiments, another cable that may, for example, include holes for attachment to the chain attachment device 410 may be used. Further, although the sleeve 802 is shown to have a cylindrical shape, in alternative embodiments, the sleeve 802 may have other shapes without departing from the scope of this disclosure. Further, in some alternative embodiments, the vessel 404 may have shapes other than shown in FIG. 8. For example, the vessel 404 may have at least one flat surface such that the sleeve 802 comes in contact with the flat surface of the vessel 404 instead of the curved surface shown in FIG. 8. In some example embodiments, the vessel 404 may be positioned in a different orientation such as a vertical orientation instead of the horizontal orientation shown in FIG. 8.

Figure 9:
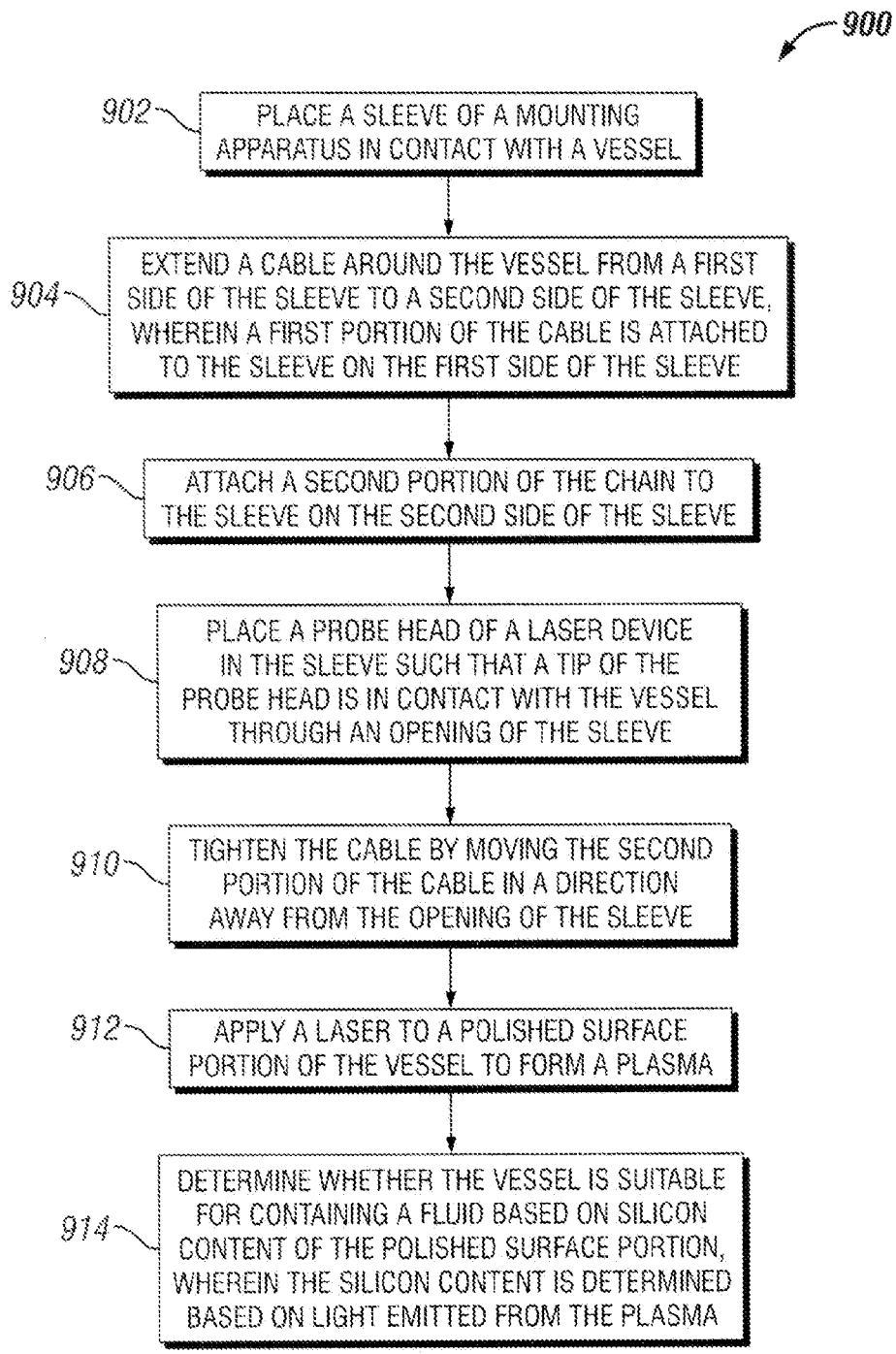
FIG. 9 illustrates a flow chart of a method for evaluating a vessel for suitability to contain a fluid based on silicon content of the vessel using the portable laser device of FIG. 1 and the mounting apparatus of FIG. 4 or FIG. 8 according to an example embodiment.

FIG. 9 illustrates a flow chart of a method for evaluating a vessel for suitability to contain a fluid based on silicon content of the vessel using the portable laser device of FIG. 1 and the mounting apparatus of FIG. 4 or FIG. 8 according to an example embodiment. Referring to FIGS. 4, 5, 8, and 9, in some example embodiments, the method 900 includes placing a sleeve of a mounting apparatus in contact with a vessel, at step 902. For example, the sleeve 402 or 802 may be placed in contact with the vessel 404 as shown in FIGS. 4 and 8. At step 904, the method 900 includes extending a cable around the vessel from a first side of the sleeve to a second side of the sleeve. A first portion of the cable may be attached to the sleeve on the first side of the sleeve. For example, the first portion 804 of the chain 406 may be attached to the chain attachment device 418, which is attached to the sleeve 402 or 802. The chain 406 may be extended around a portion of the vessel 404 as shown in FIGS. 4, 5, and 8.

At step 906, the method 900 includes attaching a second portion of the cable to the sleeve on the second side of the sleeve. To illustrate, after the chain 406 is extended around the vessel 404, the second portion 428 of the chain 406 may be attached to the chain attachment device 410 that is attached to the sleeve 402 or 802. At step 908, the method 900 includes placing a probe head of a laser device in the sleeve such that a tip of the probe head or a curved tip attached to the probe head is in contact with the vessel through an opening of the sleeve. For example, the probe head 102 is shown positioned in the cavity 426 of the sleeve 402 in FIG. 5.

As shown in FIG. 5, the curved tip 502 may be in contact with the vessel 404. For example, prior to placing the probe in the sleeve at step 908, the method 900 may include forming a polished surface portion of the vessel to remove oxidation from a portion of the vessel. In some example embodiments, to determine whether an adequately polished surface portion is formed, polishing of a surface may be and checking for silicon content may be repeated until a consistent weight percent of silicon is determined. The passageway 602 of the curved tip 502 shown in FIG. 6 is positioned over the polished surface portion of the vessel 404 such that laser from the laser device 100 of FIG. 1 can be applied to the polished surface portion and such that light emitted from the plasma resulting from the laser can reach the collection optics 112 of the laser device 100 of FIG. 1. The probe head 102 is also shown positioned in the cavity of the sleeve 802 in FIG. 8 such that the tip of the probe head 102 is in contact with the vessel 404. In FIG. 8, the opening of the probe head 102 is positioned against the polished surface portion of the vessel 404 such that a focused laser beam from the laser device 100 of FIG. 1 can be applied to the polished surface portion and light from the plasma resulting from the laser can enter the collection optics 112.

At step 910, the method 900 includes tightening the cable by moving the second portion of the cable in a direction away from the opening of the sleeve. For example, the length adjustment screw 408 shown in FIG. 4 may be rotated (for example, using a wrench) such that the chain attachment device 410 moves up along the length adjustment screw 408 pulling the second portion 428 of the chain 406 up, which results in the tightening of the chain 406 around the vessel 404.

At step 912, the method 900 includes applying a laser to a polished surface portion of the vessel to form plasma. As described above, the laser device 100 may be used to apply a laser (e.g., laser pulses) to the polished surface portion of the vessel 400. At step 914, the method 900 includes determining whether the vessel is suitable for containing a fluid based on silicon content of the polished surface portion, for example, as described with respect to the method 200 of FIG. 2. As described with respect to the method 200, the silicon content is estimated based on light emitted from the plasma. For example, determining whether the vessel is suitable for containing the fluid may include determining whether the silicon content of the polished surface portion is at least 0.10 weight percent, for example, when the vessel is made from carbon steel. In some example embodiments, the method 900 may be implemented to a vessel at various temperatures including elevated temperatures (e.g., 400° F.).

In some example embodiments, the method 900 may be performed on different sections of a vessel. To illustrate, a vessel may include several components. For example, a pipe may include many pieces of pipe, elbows, etc. that are, for example, welded together. Although a particular order of steps of the method 900 are shown in FIG. 9, in some alternative embodiments, the steps may be performed in a different order without departing from the scope of this disclosure.

Although some embodiments have been described herein in detail, the descriptions are by way of example. The features of the embodiments described herein are representative and, in alternative embodiments, certain features, elements, and/or steps may be added or omitted. Additionally, modifications to aspects of the embodiments described herein may be made by those skilled in the art without departing from the spirit and scope of the following claims, the scope of which are to be accorded the broadest interpretation so as to encompass modifications and equivalent structures.

What is claimed is:

1. A method for evaluating a vessel for suitability to contain a fluid, the method comprising:
   providing a vessel;
   forming a polished surface portion of the vessel by removing oxidation and/or one or more contaminants from a portion of the vessel;
   placing a sleeve of a mounting apparatus in contact with a vessel;
   placing a probe head of a laser device in the sleeve such that a tip of the probe head is in contact with the polished surface portion of the vessel through an opening of the sleeve;
   applying, after the probe head is in contact with the polished surface portion of the vessel through the opening of the sleeve, a focused laser from the laser device to the polished surface portion to form a plasma on the polished surface portion; and
   determining whether the vessel is suitable for containing a fluid based on silicon content of the polished surface portion, wherein the silicon content is determined based on light emitted from the plasma.

2. The method of claim 1, wherein the silicon content is estimated based on an intensity level of the light emitted from the plasma and compared to a calibration curve.

3. The method of claim 2, wherein a calibration curve is generated from light intensity-versus-wavelength calibration spectra based on a component containing a respective known weight percentage of silicon and wherein different emission spectra correspond to different weight percentages of silicon.

4. The method of claim 2, wherein a portion of each calibration curve that corresponds to a wavelength range of approximately 288.15 nanometer (nm) to approximately 288.3 nm is used to determine whether the silicon content of the polished surface portion is at least a threshold weight percent.

5. The method of claim 1, further comprising:
   determining intensity level of existing light prior to applying the focused laser to the polished surface portion; and
   subtracting the intensity level of existing light from intensity level of light determined after applying the focused laser to determine the intensity level of the light emitted from the plasma.

6. The method of claim 1, wherein the vessel is used in a sulfidation service.

7. The method of claim 6, wherein determining whether the vessel is suitable for containing the fluid comprises determining whether the silicon content of the polished surface portion is at least 0.10 weight percent.

8. The method of claim 1, wherein applying the focused laser to the polished surface portion includes applying a laser pulse once every three seconds, wherein the laser pulse has a width of between 5 nanoseconds and 8 nanoseconds.

9. The method of claim 8, wherein the laser pulse has approximately 25 millijoules of energy.

10. The method of claim 8, wherein applying the focused laser to the polished surface portion includes applying ten laser pulses.

11. A method for evaluating a vessel for suitability to contain a fluid, the method comprising:
   placing a sleeve of a mounting apparatus in contact with a vessel;
   extending a cable around the vessel from a first side of the sleeve to a second side of the sleeve, wherein a first portion of the cable is attached to the sleeve on the first side of the sleeve;
   attaching a second portion of the cable to the sleeve on the second side of the sleeve;

placing a probe head of a laser device in the sleeve such that a tip of the probe head is in contact with the vessel through an opening of the sleeve;

tightening the cable by moving the second portion of the cable in a direction away from the opening of the sleeve;

applying a laser to a polished surface portion of the vessel to form a plasma; and determining whether the vessel is suitable for containing a fluid based on silicon content of the polished surface portion, wherein the silicon content is estimated based on light emitted from the plasma.

12. The method of claim 11, further comprising forming a polished surface portion of the vessel to remove oxidation and/or one or more contaminants from a portion of the vessel.

13. The method of claim 12, further comprising applying a focused laser to the polished surface portion to form a plasma on the polished surface portion.

14. The method of claim 11, wherein the vessel has a temperature of up to or 450° F. or greater.

15. The method of claim 11, wherein determining whether the vessel is suitable for containing the fluid comprises determining whether the silicon content of the polished surface portion is at least 0.10 weight percent.

* * * * *